United States Patent [19]
Koyama et al.

[11] Patent Number: 5,855,914
[45] Date of Patent: Jan. 5, 1999

[54] GRANULES HAVING CORE AND THEIR PRODUCTION

[75] Inventors: Hiroyoshi Koyama, Mishima-gun; Shunichi Itoh, Suita; Shin-ichiro Hirai, Kyoto, all of Japan

[73] Assignee: Takeda Chemical Industries, Ltd., Osaka, Japan

[21] Appl. No.: 287,424

[22] Filed: Aug. 9, 1994

Related U.S. Application Data

[63] Continuation of Ser. No. 100,203, Aug. 2, 1993, abandoned, which is a continuation of Ser. No. 963,253, Oct. 19, 1992, abandoned, which is a continuation of Ser. No. 412,435, Sep. 26, 1989, abandoned.

[30] Foreign Application Priority Data

Sep. 27, 1988 [JP] Japan .................................. 63-243543

[51] Int. Cl.⁶ ............................... A61K 9/16; A61K 9/36; A61K 9/62
[52] U.S. Cl. ......................... 424/494; 424/461; 424/480; 514/781
[58] Field of Search ..................................... 424/489, 490, 424/494, 461, 480

[56] References Cited

U.S. PATENT DOCUMENTS

| | | | |
|---|---|---|---|
| 3,664,963 | 5/1972 | Pasin | 424/491 |
| 4,261,971 | 4/1981 | Appelgren et al. | 424/490 |
| 4,568,559 | 2/1986 | Nuwayser et al. | 427/3 |
| 4,606,909 | 8/1986 | Bechgaard et al. | 424/21 |
| 4,704,285 | 11/1987 | Alderman | 424/468 |
| 4,871,549 | 10/1989 | Ueda et al. | 424/494 |
| 4,975,275 | 12/1990 | Kehoe | 424/48 |
| 5,026,560 | 6/1991 | Makino et al. | 424/494 |

FOREIGN PATENT DOCUMENTS

| | | |
|---|---|---|
| 200902 | 12/1986 | European Pat. Off. . |
| 277741 | 10/1988 | European Pat. Off. . |
| 2103486 | 2/1983 | United Kingdom . |

*Primary Examiner*—Thurman K. Page
*Assistant Examiner*—James M. Spear
*Attorney, Agent, or Firm*—Foley & Lardner

[57] ABSTRACT

Granules having a core are produced by spraying core granules with a dispersion of a low substituted hydroxypropylcellulose (L-HPC), and, if necessary, simultaneously applying a dusting powder. The granules having a core thus obtained exhibit increased granule strength and improved disintegrating property as compared with those produced by known methods. An active ingredient such as a drug can be contained in the dispersion, dusting powder or core granules.

18 Claims, No Drawings

GRANULES HAVING CORE AND THEIR PRODUCTION

This application is a continuation of U.S. application Ser. No. 08/100,203 filed Aug. 2, 1993. A now abandoned, which is a continuation of U.S. application Ser. No.07/963,253 filed Oct. 19, 1992, now abandoned which is a continuation of U.S. application Ser. No. 07/412,435 filed Sept. 26, 1989 now abandoned.

This invention relates to granules having a core, which exhibit increased granule strength and improved disintegrating property, thus being usable in such areas as foods and pharmaceuticals, and to a process for the production thereof.

In recent years, a great number of investigations has been carried out on the drug-release controlled system (or the drug delivery system). As far as the form of oral preparation is concerned, so-called coated granules consisting of granules being provided with a variety of coatings have come into frequent use, and these granules have been employed as such as granule preparations or developed in the form of capsules filled with the granules.

As the reason behind this, there are mentioned the fact that granular preparation, when compared with tablet preparation from a biopharmaceutical point of view, does not produce individual variation in gastric emptying rate, absorption, etc. and is almost free from influence by meals.

For the production of spherical granules, there has been generally known a process which involves granulation by extrusion and spherical forming by means of a marumerizer (spheronizing equipment), but the granules produced by this process, with their inferior sphericalness and widened particle size distribution, are considered difficult to be provided with uniform coating, resulting in difficulties in the manufacture of accurately drug-release controlled pharmaceutical preparations.

As a method of producing granules with improved sphericalness, on the other hand, investigation is carried out into the granulation with use of a centrifugal fluidized-bed coating-granulator (hereinafter referred to, in some instances, as "CF granulator").

The said method comprises providing onto the surface of spherical seed granules or cores, while spraying with water or a solution containing a binder and using simultaneously a dusting powder, if necessary, and can produce spherical granules with enhanced sphericalness and narrowed particle size distribution [refer to Drug Development and Industrial Pharmacy, 11 (8 ), 1523–1541 (1985) ].

In order to produce drug-release controlled preparations, the resultant spherical granules are coated on the surfaces with wax or polymers for the purpose of controlling the drug release, and as the method of providing such coatings, there are normally investigated the CF coating with use of CF granulator and fluidized coating by means of a fluidized-bed coating machine.

In the CF coating and fluidized coating, however, there frequently take place troubles such as destruction and scraping spherical granules at their initial stages, The said troubles not only damage the drug-release controlling function in the coated granular preparations but also affect greatly the production yields of spherical granules and coated granules. When the granules are distributed as a granular preparation on the market, furthermore, such granules are susceptible to fracture through the distribution channel. Consequently, polyvinyl-pyrrolidone is for example added as a binder so as to increase their granule strength. In addition, an increase in granule strength tends to result in deteriorated disintegrating property of the resultant granules, and there have been strongly demanded granules [Sakamoto et al.; "Yakuzai-gaku (Pharmacy)",45 (2), 187 (1985)]with rapid disintegration and increased strength.

The present inventors, taking such situations into consideration, conducted intensive investigation into spherical granules having increased granule strength and rapid disintegration by use of a CF granulator, and as a result, found and confirmed that low substituted hydroxypropylcellulose, when added to a spraying solution for coating to thereby perform granulation, can unexpectedly yield spherical granules having enhanced granule strength and improved disintegrating property and furthermore that there hardly takes place powder scattering during production which presents a problem in the utilization as a dusting powder of low substituted hydroxypropylcellulose. The finding culminated into this invention.

Thus, this invention relates to a process for producing granules having a core, characterized in that said process comprises spraying seed granules with a dispersion of low substituted hydroxypropylcellulose, and to granules having a core obtainable by said production process.

The low substituted hydroxypropylcellulose (hereinafter referred to, in some instances, as "L-HPC") to be used in this invention exhibits a content of hydroxypropyl group generally ranging from about 4 to 20π, preferably from 5 to 16%, more preferably from 10 to 13%. The said L-HPC may usually have an average particle size of not greater than 200 μm, preferably not greater than 100 μm, more preferably not greater than 10 μm.

The core granules to be used in this invention include, for example, spherical granules based on Nonpareil consisting of sucrose (75 weight %) coated with corn starch (25 weight %) by the per se known process and crystalline cellulose, and the core granules in themselves may be a different active ingredient other than the active ingredient contained in the dispersion or the dusting powder described hereinafter. Furthermore, such core granules may be coated with waxes or polymers to produce the cores.

The dispersion usable for spraying in this invention can be obtained by dispersing and/or dissolving uniformly L-HPC in water, organic solvents such as ethanol or mixtures thereof.

The said dispersion may have additionally the active ingredient and other additives other than L-HPC uniformly dispersed and/or dissolved therein.

The said active ingredient is not specifically limited, if it can be administered in the form of granules, and includes, for example, drug substances for the central nervous system, such as diazepam, idebenone, aspirin, ibuprofen, paracetamol, naproxen, piroxicam, diclofenac, indomethacin, sulindac, lorazepam, nitrazepam, phenytoin, acetaminophen, ethenzamide and ketoprofen; cardiovascular drugs, such as molsidomine, vinpocetine, propranolol, methyldopa, dipyridamole, furosemide, triamteren, nifedipine, atenolol, spironolactone, metoprolol, pindolol, captopril and isosorbide dinitrate; drugs for respiratory organs, such as amlexanox, dextromethorphan, theophylline, pseudoephedrine, salbutamol and guaifenesin; drugs for digestive organs, such as benzimidazole based drug substances having anti-ulcer activity being exemplified by 2-{[3-methyl-4-(2,2,2-trifluoroethoxy)-2-pyridyl 9 methyl-sulfinyl}benzimidazole (hereinafter referred to sometimes as "Compound A") and 5-methoxy-2-[(4-methoxy-3,5-dimethyl-2-pyridyl)methylsulfinyl] benzimidazole, cimetidine, ranitidine, pancreatin, bisacodyl and 5-aminosalicylic acid; antibiotics and chemotherapeutic agents, such as cephalexin, cefaclor, cefradine, amoxicillin, pivampicillin, bacampicillin, dicloxacillin, erythromycin, erythromycin stearate, lincomycin, doxycycline and trimethoprim/sulfamethoxazole; drugs for the metabolic system, such as serrapeptase, lysozyme chloride, adenosine triphosphate, glibenclamide and potassium chloride; and vitamin drugs, such as vitamin $B_1$, vitamin $B_2$, vitamin $B_6$, vitamin C and fursulthiamine.

As the said additive, there may be mentioned additives being generally formulated in the production of granules, and their examples include excipients (e.g., lactose, corn starch, sucrose, talc, crystalline cellulose, mannitol, light anhydrous silicic acid, magnesium carbonate, calcium carbonate, L-cysteine etc.), binders (e.g., pregelatinized starch, methylcellulose, carboxymethylcellulose, hydroxypropylcellulose, hydroxymethylpropylcellulose, polyvinylpyrrolidone, pullulan, dextrin, gum arabic, etc.), disintegrants (e.g., calcium carboxymethylcellulose, starches, crosslinked sodium carboxymethylcellulose, crosslinked insoluble polyvinylpyrrolidone, etc.), coloring agents (e.g., titanium oxide, ferric oxide, tar dyes, etc.) and the like and these may be used in more than two kinds.

In this invention, also, the powdered dusting powder produced by mixing uniformly the above-mentioned active ingredient with additives may be applied for dusting, while spraying the nucleus granules with the said dispersion. The said dusting powder shows generally a particle size of not greater than about 100 $\mu$Am, preferably not greater than about 50 $\mu$m.

The proportion in which L-HPC is formulated into the dispersion naturally varies depending upon the types and formulated proportions of the active ingredient and other additives to be incorporated, but generally ranges from 0.5 to 50 weight %, preferably from 5 to 30 weight % in particular. The formulated proportion of less than 0.3% generally requires a prolonged length of time to achieve the coating in an amount necessary for enhanced granule strength, because the concentration of L-HPC in the dispersion is low, and is not so especially favorable. The formulated proportion in excess of 60% brings about disturbances such as increased viscosity of the dispersion, resulting in troubles during the production of granules. Also naturally, furthermore, the formulated proportion of L-HPC in the dispersion may be varied continuously or stepwise in the course of coating in accordance with the objective. In such a case, coating is sometimes performed with a dispersion having a formulation proportion of L-HPC which usually exceeds 0.5 to 50 weight %, In cases where the active ingredient and other additives are dispersed simultaneously, further, their proportions may be varied.

Also, it is preferable that the resultant granules having enhanced strength and rapid disintegrating property generally contain L-HPC at the proportion of 0.1 to 15 weight %. A proportion of less than 0.05% is not adequate for increasing the granule strength, while a proportion in excess of 20% is not desirable, because this makes the proportions of other coating components too low.

In the following, the process for producing granules having a core according to this invention is described in more detail. Granulation is carried out, while nucleus granules are sprayed with a dispersion and/or solution of L-HPC and the active ingredient and/or additives, if necessary, and are applied for dusting with a dusting agent in the form of powder, as the case may be. When the stability of the active ingredient is no problem, the temperature of the said solution during the production does not have to be adjusted and may usually be at room temperature (1° to 30° C.). The granulated material is dried and then sieved to give spherical granules having a core with a uniform particle size. The usable sieves include, for example, sieves of 12 to 32 mesh, whereupon granules passing through 12 mesh but not through 32 mesh may be selected.

The granules having a core as produced by this procedure may be subjected to further coating by means of the per se known methods to provide the flavor masking coating, enteric coating, gastric coating or sustained-release coating, etc., and may furthermore be coated midway during the production for the purpose of stabilization, when the active ingredient is properly formulated. In addition, such granules may be filled into capsules by the per se known method, and may be mixed with other components to produce tablets.

The coating agents for the said purposes include, for example, hydroxypropylmethylcellulose, ethylcellulose, hydroxymethylcellulose, hydroxypropylcellulose, polyoxyethylene glycol, Tween 80, Pluronic F 68, castor oil, cellulose acetate phthalate, hydroxypropylmethylcellulose phthalate, hydroxypropylmethylcellulose acetate succinate, acrylic acid copolymers, carboxymethylethylcellulose, polyvinylacetal, diethylaminoaetate, shellac, waxes as well as coloring agents, such as talc, titanium oxide and ferric oxide red.

The granules having a core as obtained according to this invention show increased granule strength and improved disintegrating property. The granules having a core as compared with those produced by the dusting of L-HPC in the form of powder, furthermore involve lessened dust scattering of the active ingredient to be contained in the granules and can offer the advantages that the content of active ingredient can be retained at a constant level and that increased granule strength is achieved.

Below described are the examples, reference examples and test examples to illustrate this invention more specifically. In these examples, the starting materials are all used in the form of powder.

EXAMPLE 1

Charged into a CF granulator (CF-360, manufactured by Freund Co.) was 2700 g of Nonpareil (20 to 28 mesh), and coating was performed under 200 rpm rotor speed, while spraying with a solution of 3% (W/W) of L-HPC (degree of hydroxypropoxy group substitution: 10.0 to 13.0% (W/W), average particle size of not more than 30 Am. L-HPC having the same degree of substitution and average particle size was used in the examples and test examples) and 2% (W/W) of hydroxypropylcellulose dispersed and dissolved in 2000 ml of water at a rate of 25 ml per minute and also while dusting with 2000 g of a dusting powder (a 1:1:1:1 mixture of Compound A, magnesium carbonate, sucrose and corn starch) at a rate of 25 g/minute, to produce spherical granules having a core of 12 to 32 mesh after being sifted through a sieve.

3800 g of the resulting spherical granules having a core was placed in a fluidized coating machine Gratt WSG-15 (Gratt Co. of West Germany), and coating was performed with the inlet air temperature and product temperature being controlled at 50° C. and 40° C., respectively, while spraying at a rate of 50 ml/minute with an enteric-film solution of the following composition, to produce enteric-coated, spherical granules having a core. The resulting granules were found to be covered uniformly with the enteric coating, being free from granule breaking during coating process, and to pass the disintegration test in terms of particle size and enteric coating as stipulated in the Japanese Pharmacopoeia, 11th revised edition.

| [Enteric-film solution] | |
| --- | --- |
| Eudragit L30D-55 | 628 g |
| Talc | 192 g |
| Polyethylene glycol 6000 | 64 g |
| Titanium oxide | 64 g |
| Tween 80 | 32 g |
| Water | 4400 g |

EXAMPLE 2

Charged into a CF granulator (CF-1300, manufactured by Freund Co.) was 42 kg of Nonpareil (24 to 32 mesh), and granulation was carried out under 60 rpm rotor speed, while spraying with an in-advance prepared coating solution of the following composition at a rate of 200 ml/min.×2 guns. The resulting granulated material was dried under vacuum at 40° C. for 16 hours and subjected to sifting through a sieve to produce spherical granules having a core, of 12 to 32 mesh.

| [Coating solution] | |
| --- | --- |
| Serrapeptase | 3000 g |
| L-HPC | 1600 g |
| Lactose | 160 g |
| Sucrose | 1600 g |
| Talc | 1600 g |
| Ethanol | 11500 g |
| Water | 9700 g |

48 kg of the resultant spherical granules having a core was charged in a fluidized coating machine (FLO-60, manufactured by Freund/Okawara Co.), in which the inlet air and outlet air exhausting temperatures were controlled at 60° C. and 40° C., respectively, and coating was performed, while spraying an in advance prepared enteric-film solution of the following composition at a rate of 170 g/min.×3 guns, to produce enteric-coated, spherical granules having a core. The resulting granules were found to be free from granule breaking during coating, being covered uniformly with the enteric film, and to pass the disintegration test in terms of particle size and enteric coating as stipulated in the Japanese Pharmacopoeia, 11th revised edition.

| [Enteric-film solution] | |
| --- | --- |
| hydroxypropylmethylcellulose phthalate 220824 | 11600 g |
| Shellac | 2800 g |
| Polyethylene glycol 6000 | 660 g |
| Ethanol | 56300 g |
| Acetone | 131500 g |

420 g of the enteric-coated, spherical granules having a core as obtained by the above procedure, 270 g of aluminum hydroxide sodiumhydrogencarbonate coprecipitate, 580 g of crystalline cellulose, 150 g of crosslinked sodium carboxymethylcellulose, 20 g of magnesium stearate and 1440 g of granules for tablet compression as prepared in advance by the below-described procedure were blended in a tumbler type mixing machine (TM-15, manufactured by Showa Kagaku-Kikai Manufacturing Co.) for 3 minutes (blending conditions: 10 rpm for 3 minutes). The blended mixture was compressed into tablets at a compression pressure of 1 ton/cm$^2$, employing Pure Press Correct 19K (manufactured by Kikusui Seisakusho Co.), with the use of an oblong type punch, to give white plain tablets each having a weight of 480 mg, 15 mm of major axis, 6.5 mm of minor axis, 6.4 mm of thickness and 1.2 minutes of disintegration time.

[Granules for Tablet Compression]

A mixture consisting of 900 mg of acetaminophen, 7.5 g of chlorpheniramine maleate, 48 g of noscapine, 75 g of anhydrous caffeine, 24 g of dihydrocodeine phosphate, 60 g of dl-methylephedrine hydrochloride, 72 g of crosslinked sodium carboxymethylcellulose and 72 g of corn starch was admixed with crystalline cellulose to make up to 1389.6 g, which was mixed adequately in a vertical granulator (FM-G25 type, manufactured by Fuji Sangyo Co.)(mixing conditions: 400 rpm, 15 minutes) and kneaded with an aqueous solution containing 50.4 g of hydroxypropylcellulose dissolved therein. The resulting white kneaded material was dried in a fluidized dryer (FD-3S, manufactured by Fuji Sangyo Co.) at the inlet air temperature of 60 ° C. for 30 minutes and sieved through a 1.5 mm punching screen by use of power mill (P-3 type, manufactured by Showa Kagaku-Kikai Manufacturing Co.) to give granules for tablet compression.

EXAMPLE 3

Placed into a Mini-CF granulator (manufactured by Freund Co.) was 85 g of Nonpareil (24 to 32 mesh), and granulation was carried out under 400 rpm rotor speed, while spraying with a solution prepared by dispersing and/or dissolving respectively 30% (W/W) of L-HPC and 1% (W/W) of hydroxypropylcellulose in 50 g of ethanol at a rate of 2.5 g/minute and while applying with a dusting powder prepared by mixing 10 g of idebenone, 10 g of sucrose and 30 g of corn starch uniformly at a rate of 5 g/minute, followed by spraying continuously with the coating solution, to produce a granulated material. The granulated material was dried under vacuum at 40° C. for 16 hours and sifted through a sieve to give spherical granules having a core, of 12 to 32 mesh. 240 mg of the said granules was filled into a hard capsule of No. 2 (Weight: 65 g) by use of a capsule filling machine (manufactured by Parke-Davis Co.) to produce a capsule.

EXAMPLE 4

Placed into a Mini-CF granulator (manufactured by Freund Co.) was 85 g of Nonpareil (24 to 32 mesh), and granulation was performed under 400 rpm rotor speed, while spraying, at a rate of 2.5 g/minute, with a coating solution prepared by dispersing 5 g of L-HPC and 4 g of talc in 50 g of water and then dissolving furthermore 6 g of fursulthiamine hydrochloride, 4 g of sucrose and 1 g of hydroxypropylcellulose to produce a granulated material. The granulated material was dried under vacuum at 40 ° C. for 16 hours and sifted through a sieve to give spherical granules having a core, of 12 to 32 mesh.

EXAMPLE 5

Granulation was carried out with use of the coating solutions of different compositions which were prepared based on the coating solution used in Example 2 by varying the amounts of L-HPC and sucrose respectively as shown below in the table according to the initial, middle and final stages of coating. The resulting granules having a core were found to be free from granule breaking during coating, being covered uniformly with the enteric films, and to pass the disintegration test in terms of particle size and enteric coating as stipulated in the Japanese Pharmacopoeia, 11th revised edition.

[Amount of L-HPC and sucrose in the coating solutions]

|  | Initial stage of coating | Middle stage of coating | Final stage of coating |
|---|---|---|---|
| L-HPC | The same as the amount of Example 2 | Double the amount of Example 2 | Half the amount of Example 2 |
| Sucrose | The same as the amount of Example 2 | Half the amount of Example 2 | Double the amount of Example 2 |

REFERENCE EXAMPLE 1

In the procedure of Example 4, fursulthiamine hydrochloride L-HPC, sucrose and talc were eliminated in the coating solution, and fursulthiamine hydrochloride L-HPC, sucrose and talc were mixed uniformly to produce a dusting powder. Coating was carried out by applying the dusting powder at a rate of 1.2 g/minute, while spraying with the coating solution at a rate of 3 g/minute, and after vacuum drying at 40° C. for 16 hours, sifting was performed through a sieve to five spherical granules having a core, of 12 to 32 mesh.

REFERENCE EXAMPLE 2

In the procedure of Example 4, granulation was conducted with the use of the coating solutions prepared by utilizing, in place of L-HPC in the coating solution, crystalline cellulose, corn starch, pregelatinized starch, hydroxypropylcellulose, pullulan, carboxymethylcelluose or lactose, respectively, to produce spherical granules having core. The granules were sifted through a sieve to give spherical granules having a core, of 12 to 32 mesh.

TEST EXAMPLE 1

Individually placed in a stainless steel cylinder of a 50-ml capacity (inner content of 50 ml, diameter of 32 mm) were 5 g each of the said granules (12 to 32 mesh) as obtained in Examples 4 and 5 and Reference Examples 1 and 2, and shaking was effected by use of Spex mill (manufactured by Spex Co. of West Germany) for 15 minutes. Then sifting was conducted through a 32-mesh sieve, and the amounts not having passed through the sieve were measured to determine the ratios of the granules not passed through the sieve, which were taken as a granule strength. Furthermore, the disintegration times of the granules were measured in accordance with the disintegration test method of the Japanese Pharmacopeia (11th revised edition). The results indicate that the granules having a core according to this invention possessed increased strength and improved disintegrating property.

TABLE 1

[Granule strength and disintegration time]

| Example No. | Test component | Granule strength | Disintegration time |
|---|---|---|---|
| Example 4 | L-HPC | 98% | 1 min. |
| Example 5 | L-HPC (varied amount) | 98% | 1 min. |
| Ref. Ex. 1 | L-HPC (dusting powder) | 95% | 1 min. |
| Ref. Ex. 2 | Crystalline cellulose | 95% | 2 min. |
|  | Corn starch | 70% | 1 min. |
|  | Pregelatinized starch | 88% | 30 min. or more |
|  | Hydroxypropylcellulose | 93% | 15 min. |

TABLE 1-continued

[Granule strength and disintegration time]

| Example No. | Test component | Granule strength | Disintegration time |
|---|---|---|---|
|  | Pullulan | 83% | 2 min. |
|  | Carboxymethylcellulose | 80% | 2 min. |
|  | Lactose | 75% | 1 min. |

Test Example 2

Comparison was made between the granules obtained in Example 4 and Reference Example 1 (control) in terms of yield and content of fursulthiamine hydrochloride, and the results in Table 2 revealed that the granules of Example 4 showed higher yield and fursulthiamine hydrochloride content than the ones of Reference Example 1, and confirmed that the production process of this invention hardly caused dust scattering of the principal medicament during production.

TABLE 2

[Yield of granules and content of fursulthiamine hydrochloride]

|  | Yield | Content |
|---|---|---|
| This invention | 103 g | 99% |
| Control | 99 g | 96% |

We claim:

1. A method for producing granules having a core and having an increased granule strength, wherein the method consists essentially of (a) spraying seed granules with a dispersion or solution of low substituted hydroxypropyl cellulose, and (b) drying the granulated material to obtain granules containing said low substituted hydroxypropyl cellulose at a proportion of 0.1 to 15 weight percent based on the weight of the granule.

2. A method for producing granules having a core and having an increased granule size, wherein the method consists essentially of (a) spraying seed granules with a dispersion or solution of low subsitituted hydroxypropyl cellulose, (b) applying a dusting agent in the form of powder while the seed granules are being sprayed with the dispersion or solution, and (c) drying the granulated material.

3. A method according to claim 2, wherein the dusting agent is incorporated with an active ingredient.

4. A method according to claim 1, wherein the proportion is 10 to 13 weight percent.

5. A method according to claim 3, wherein the active ingredient is a drug.

6. A method according to claim 1, wherein the dispersion or solution consists essentially of said hydroxypropyl cellulose.

7. A method according to claim 1, wherein the hydroxypropyl cellulose contains 5 to 16% by weight of hydroxypropyl groups.

8. Granules produced by a method according to claim 1.

9. A method according to claim 1, wherein the produced granules further comprise an active ingredient.

10. A method according to claim 1, wherein the dispersion or solution further comprises an active ingredient.

11. A method according to claim 1, which consists of steps (a) and (b).

12. A method according to claim 2, which consists of steps (a), (b), and (c).

13. A method according to claim 2, wherein the proportion is 10 to 13 weight percent.

14. A method according to claim 2, wherein the dispersion or solution consists essentially of said hydroxypropyl cellulose.

15. A method according to claim 2, wherein the hydroxypropyl cellulose contains 5 to 16% by weight of hydroxypropyl groups.

16. Granules produced by a method according to claim 2.

17. A method according to claim 2, wherein the produced granules further comprise an active ingredient.

18. A method according to claim 2, wherein the dispersion or solution further comprises an active ingredient.

* * * * *